United States Patent
Nachefski

(10) Patent No.: US 9,198,980 B1
(45) Date of Patent: *Dec. 1, 2015

(54) AIR CONDITIONER MISTER, APPARATUS AND METHOD

(75) Inventor: William S. Nachefski, Fresno, TX (US)

(73) Assignee: ENVIRONMYST LLC, Houston, TX (US)

(*) Notice: Subject to any disclaimer, the term of this patent is extended or adjusted under 35 U.S.C. 154(b) by 498 days.

This patent is subject to a terminal disclaimer.

(21) Appl. No.: 13/482,815

(22) Filed: May 29, 2012

(51) Int. Cl.
*F25B 39/04* (2006.01)
*A61K 48/00* (2006.01)

(52) U.S. Cl.
CPC .......... *A61K 48/00* (2013.01); *F25B 2339/047* (2013.01)

(58) Field of Classification Search
CPC ................................................. F25B 2339/047
USPC ....................................... 62/91, 171, 183, 305
See application file for complete search history.

(56) References Cited

U.S. PATENT DOCUMENTS

| | | | | |
|---|---|---|---|---|
| 5,419,147 A | * | 5/1995 | Cooper | 62/171 |
| 6,655,162 B2 | * | 12/2003 | McKee | 62/171 |
| 6,837,065 B2 | | 1/2005 | Permetti | |
| 7,441,412 B2 | | 10/2008 | Jensen | |
| 2008/0104980 A1 | * | 5/2008 | Payton | 62/171 |
| 2010/0229586 A1 | * | 9/2010 | Nicodem | 62/305 |

OTHER PUBLICATIONS

United States Patent and Trademark Office, Notice of Allowance and Fee(s) Due, U.S. Appl. No. 14/495,466, which is the US child to the instant application, May 13, 2015.

* cited by examiner

*Primary Examiner* — Jonathan Bradford
(74) *Attorney, Agent, or Firm* — Howard L. Speight, PLLC

(57) ABSTRACT

A method and apparatus for increasing the efficiency of an air conditioning system. Misting the air conditioning system's condenser with water cools the condenser and enables the system to more rapidly condense the refrigerant therein. By increasing the rate at which the refrigerant is condensed, energy and wear and tear on the system is reduced. Control of the misting is important, and sensing environmental and other present metrics to assist that control increases the efficiency offered by the present method and apparatus.

12 Claims, 5 Drawing Sheets

AIR CONDITIONER MISTER, APPARATUS AND METHOD

BACKGROUND OF THE INVENTION

The present invention relates generally to an apparatus and method for cooling an air conditioner system in order to boost the efficiency thereof. In order to better understand the invention, some background on the operation of an air conditioner system may be helpful.

Willis Haviland Carrier developed the first modern air conditioning system in 1902. It was designed to solve a humidity problem at the Sackett-Wilhelms Lithographing and Publishing Company in Brooklyn, N.Y. Paper stock at the plant would sometimes absorb moisture from the warm summer air, making it difficult to apply the layered inking techniques of the time. Carrier treated the air inside the building by blowing it across chilled pipes. The air cooled as it passed across the cold pipes, and since cool air cannot carry as much moisture as warm air, the process reduced the humidity in the plant and stabilized the moisture content of the paper. Reducing the humidity also had the side benefit of lowering the air temperature, and a new technology was born.

The actual process air conditioners use to reduce the ambient air temperature in a room is based on a simple scientific principle. The rest is achieved with the application of a few clever mechanical techniques. Air conditioners use refrigeration to chill indoor air, taking advantage of a physical law—when a liquid converts to a gas (in a process called phase conversion), it absorbs heat. Air conditioners exploit this feature of phase conversion by forcing special chemical compounds to evaporate and condense over and over again in a closed system of coils.

The compounds involved are refrigerants that have properties enabling them to change at relatively low temperatures. Air conditioners also contain fans that move warm interior air over these cold, refrigerant-filled coils. In fact, central air conditioners have a whole system of ducts designed to funnel air to and from these serpentine, air-chilling coils.

When hot air flows over the cold, low-pressure evaporator coils, the refrigerant inside absorbs heat as it changes from a liquid to a gaseous state. To keep cooling efficiently, the air conditioner has to convert the refrigerant gas back to a liquid again. To do that, a compressor puts the gas under high pressure, which is a process that creates unwanted heat. All the extra heat created by compressing the gas is then evacuated to the outdoors with the help of a second set of coils called condenser coils, and a second fan. As the gas cools, it changes back to a liquid, and the process starts all over again. The process can be thought of as an endless cycle: liquid refrigerant, phase conversion to a gas, heat absorption, compression, and phase transition back to a liquid again.

The major parts of an air conditioner manage refrigerant and move air in two directions: indoors and outside. The parts consist of:
Evaporator—Receives the liquid refrigerant;
Condenser—Facilitates heat transfer;
Expansion valve—regulates refrigerant flow into the evaporator;
Compressor—A pump that pressurizes refrigerant.

The cold side of an air conditioner contains the evaporator and a fan that blows air over the chilled coils and into the room. The hot side contains the compressor, condenser, and another fan to vent hot air coming off the compressed refrigerant to the outdoors. In between the two sets of coils, there typically is an expansion valve. It regulates the amount of compressed liquid refrigerant moving into the evaporator. Once in the evaporator, the refrigerant experiences a pressure drop, expands, and changes back into a gas. The compressor typically is an electric pump that pressurizes the refrigerant gas as part of the process of turning it back into a liquid. There are some additional sensors, timers and valves, but the evaporator, compressor, condenser, and expansion valve are the main components of an air conditioner.

Most air conditioners have their capacity rated in British thermal units (Btu). A Btu is the amount of heat necessary to raise the temperature of 1 pound (0.45 kilograms) of water one degree Fahrenheit (0.56 degrees Celsius). One Btu equals 1,055 joules. In heating and cooling terms, one ton equals 12,000 Btu.

A typical window unit air conditioner might be rated at 10,000 Btu. For comparison, a typical 2,000-square-foot (185.8 square meters) house might have a 5-ton (60,000-Btu) air conditioning system, implying that a person might need perhaps 30 Btu per square foot. These are rough estimates. The energy efficiency rating (EER) of an air conditioner is its Btu rating over its wattage. As an example, if a 10,000-Btu air conditioner consumes 1,200 watts, its EER is 8.3 (10,000 Btu/1,200 watts). Obviously, one would like the EER to be as high as possible, but normally a higher EER is accompanied by a higher price.

The following example helps illustrate the process of selecting the most economical/efficient air conditioning system. Suppose you have a choice between two 10,000-Btu units. One has an EER of 8.3 and consumes 1,200 watts, and the other has an EER of 10 and consumes 1,000 watts. Suppose also that the price difference between the two units is $100. To determine the payback period on the more expensive unit, you need to know approximately how many hours per year you will be operating the air conditioner and how much a kilowatt-hour (kWh) costs in your area. Assume you plan to use the air conditioner six hours a day for four months of the year, at a cost of $0.10/kWh. The difference in energy consumption between the two units is 200 watts. This means that every five hours the less expensive unit will consume one additional kWh (or $0.10) more than the more expensive unit.

With roughly 30 days in a month, you are operating the air conditioner:

$$4 \text{ months} \times 30 \text{ days per month} \times 6 \text{ hours per day} = 720 \text{ hours}$$

$$[(720 \text{ hours} \times 200 \text{ watts})/(1000 \text{ watts/kilowatt})] \times \$0.10/\text{kilowatt hours} = \$14.40$$

The more expensive air conditioning unit costs $100 more to purchase but less money to operate. In our example, it will take seven years (7×$14.40=$100.80) for the higher priced unit to break even. Because of the rising costs of electricity and a growing trend to "go green," more people are turning to alternative cooling methods to spare their pocketbooks and the environment. Nevertheless, as the above description shows, substantial savings can also be had by increasing the efficiency of an existing air conditioner unit. One way of doing that is by employing the method and apparatus of the present invention, which uses less energy to achieve the same or greater performance.

SUMMARY OF THE INVENTION

The present invention provides an alternative to the ever-increasing cost of electricity and the corresponding cost burden of using an air conditioner. As described in more detail below, the present invention reduces the amount of energy needed to condense the refrigerant on the hot side of the air conditioning system. Specifically, the present invention provides a novel system for spraying a mist of water on the air conditioner's condensing coils so that, as the water hits the coils and evaporates, it reduces the temperature of the coils. This reduced temperature assists in more rapidly reducing the temperature of the refrigerant inside the condenser and more rapidly enables the refrigerant to change from a gas to a liquid. The more rapidly this process takes place, the less electricity needed (by the compressor, fan, etc.) to complete that process. The less electricity needed, the less the cost to run the system. Likewise, the less the compressor and fan are required to run to do their job, the longer they will last and not need to be replaced.

DETAILED DESCRIPTION OF THE INVENTION

Figure 1:
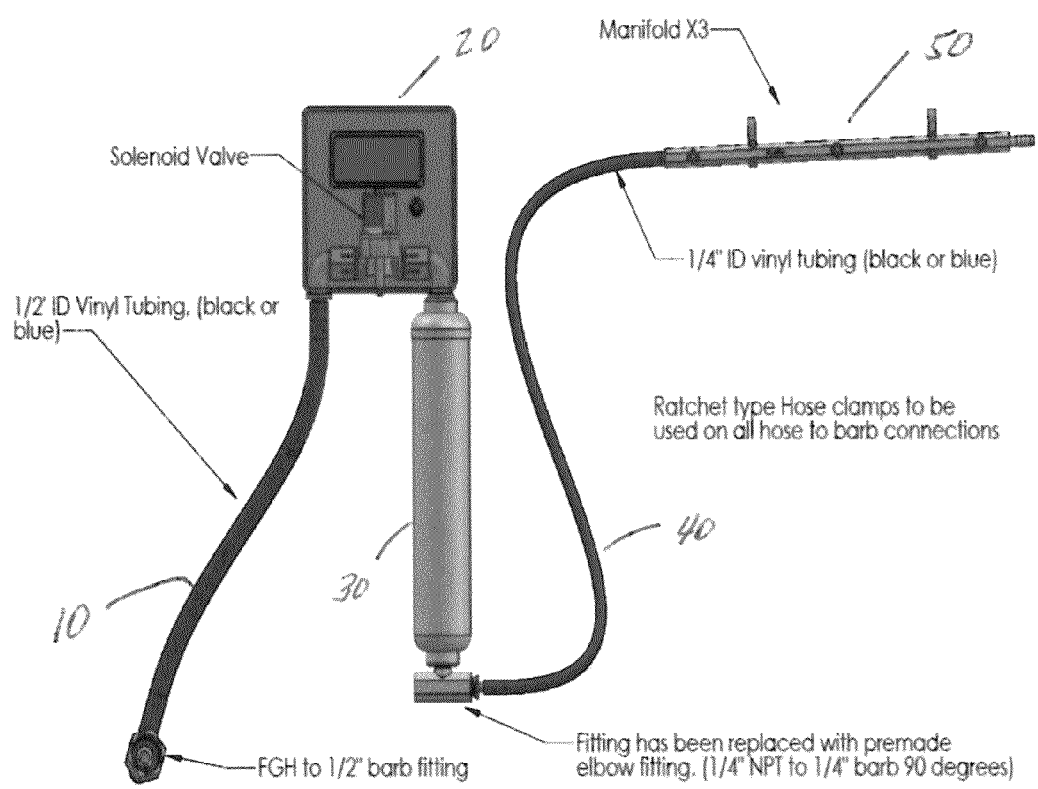
FIG. 1 illustrates a preferred embodiment of the present invention including a supply hose, control unit, filter, and manifold.

Referring to FIG. 1, a preferred embodiment of the present invention is illustrated. FIG. 1 shows an embodiment of the present invention including first supply hose 10, control box 20, filter 30, second supply hose 40, and manifold 50. The first supply hose preferably is constructed from ½ inch vinyl tubing and connects to a water supply source at a first end and to an input on control box 20 at a second end. Control box 20 houses at least a solenoid valve and circuitry programmable to control operation of the present invention. A first end of filter 30 connects to an output of control box 20, whereas a second end of filter 30 connects to a first end of second supply hose 40. Supply hose 40 preferably is constructed from ¼ inch vinyl tubing. A second end of supply hose 40 connects to manifold 50.

Figure 2:
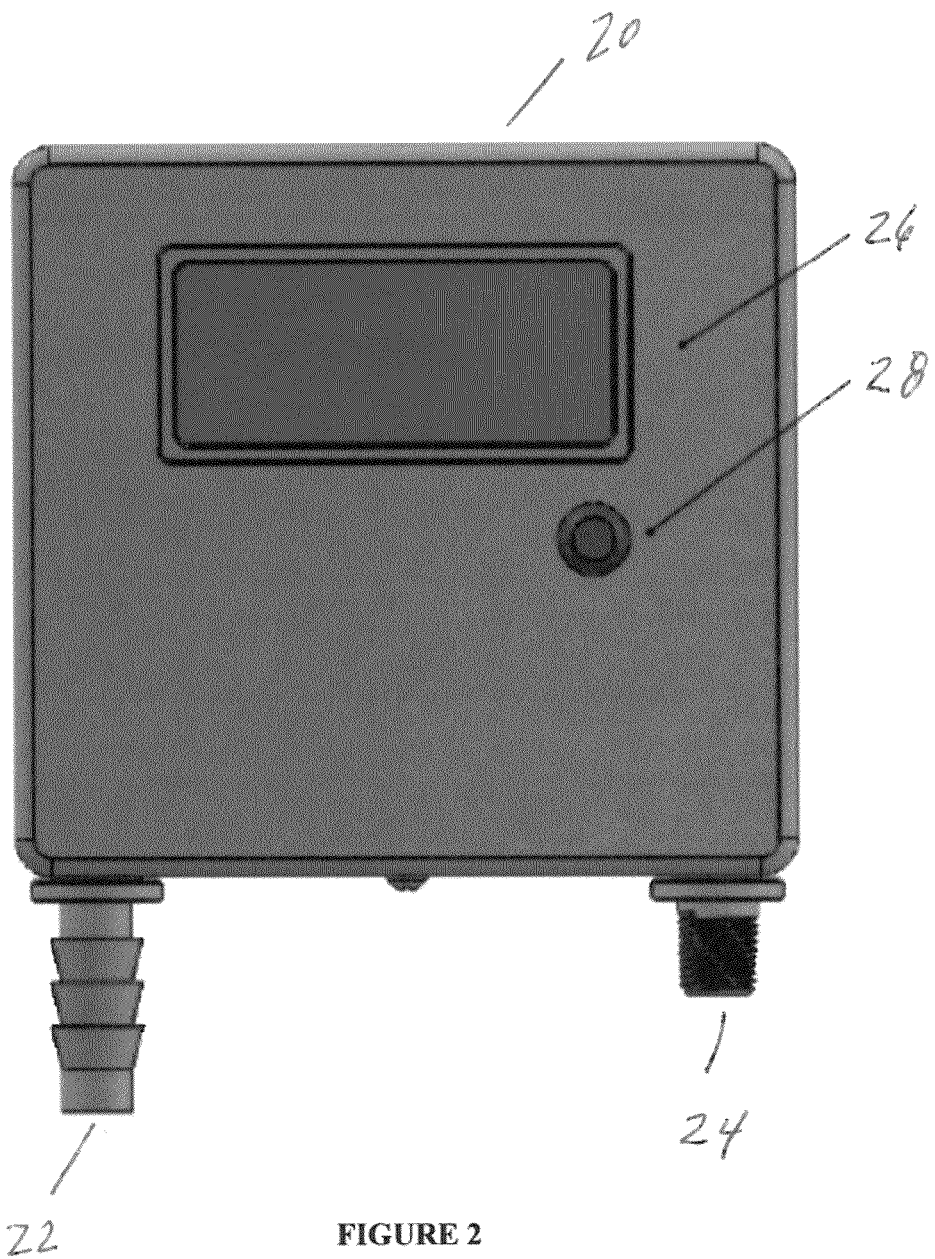
FIG. 2 illustrates an isolated view of the control box.

Referring to FIG. 2, a preferred embodiment of control box 20 is illustrated. As shown, control box 20 includes input 22, output 24, button selector 28, and LCD view screen 26.

Figure 3:
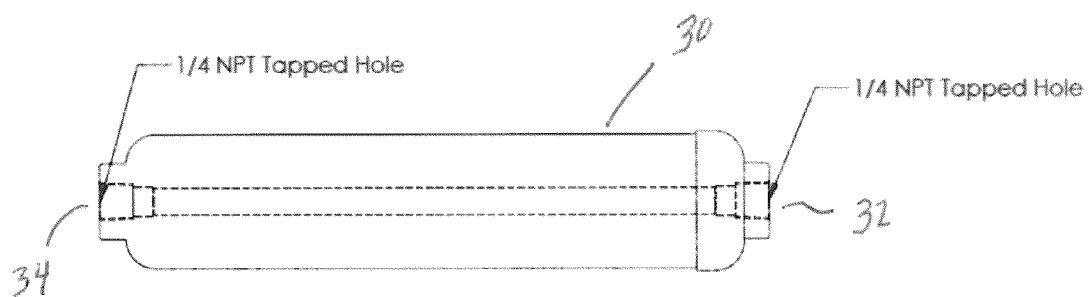
FIG. 3 illustrates an isolated view of the filter.

Referring to FIG. 3, a preferred embodiment of filter 30 is illustrated. As shown, filter 30 includes input 32 and output 34.

Figure 4:
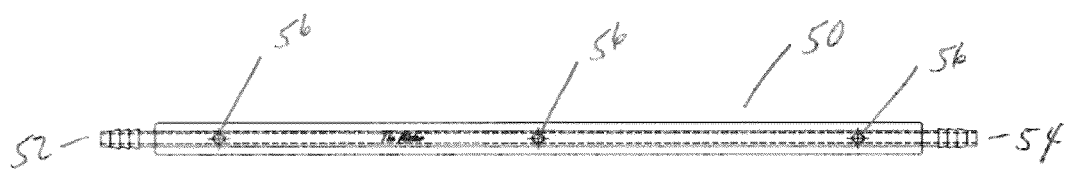
FIG. 4 illustrates an isolated view of the manifold.

Referring to FIG. 4, a preferred embodiment of manifold 50 is illustrated. As shown, manifold 50 includes input 52, output 54, and spray nozzles 56. While three spray nozzles 56 are depicted, different numbers can be chosen depending on the need for the particular application.

The system depicted in FIG. 1 operates as follows. The first end of supply hose 10 is connected to a water source, such as a water faucet on the exterior of a home. When the water supply is turned on, water flows from the source, through first supply hose 10, and into control box 20. Control box 20 includes a solenoid valve that opens and closes under the program control of control box 20. When the solenoid valve is closed, no water flows through control box 20. When the solenoid valve is open, water flows through control box 20 and into filter 30.

As will be described in more detail below, filter 30 softens the water flowing there-through so as to reduce mineral build-up in second supply hose 40, manifold 50, and on any surface in the air conditioner unit that gets wet as a result of using the apparatus. An advantage to locating filter 30 on the downstream side of control box 20 is that it is not under constant water pressure, as it would be if it were located on the upstream side of control box 20. This advantageously extends the life of filter 30.

Next, as water flows through filter 30 and second supply hose 40, it enters manifold 50. The water at this point is under pressure from its supply and the reduced diameter of the second supply hose. Obviously, other methods are well known for adjusting the pressure of the water supplied to manifold 50. Water enters manifold 50 and exists, under pressure, spray nozzles 56. Manifold 50 is positioned on the air conditioner system so that the exiting water spray primarily falls on the air conditioner's condenser unit. As explained above, this water and its evaporation cool the condenser, thereby aiding in the cooling of the refrigerant inside, and reducing the time/power necessary to cool the refrigerant.

As will be appreciated by those skilled in the art, one or more manifolds 50 can be employed depending on the configuration desired. For example, a single manifold 50 can be used on one side of the air conditioner unit. Alternatively, additional manifold units 50 can be connected together by uniting them at their inputs/outputs shown in FIG. 4. For example, using four manifold units 50 would enable a user to place one manifold on each of the four sides of an air conditioner so that the water spray would enter the air conditioner from all sides. Depending on the configuration, this may add to the volume of water falling on the condenser inside the air conditioner unit. Likewise, more than one manifold unit could be placed on the same side of the air conditioner if that proved to be the best way of misting the condenser.

Another option included as an embodiment of the present invention is adding a drain valve between filter 30 and manifold 50. This drain valve would open when the system is not on in order to drain water from manifold 50, second supply hose 40, and filter 30.

The time that the unit operates is also important. For example, no water should be flowing if the air conditioner unit is not running. This control of the water supply is managed by programmable circuitry inside control box 20 (in order to open/close the solenoid valve) with the aid of one or more of the inputs/metrics shown in FIG. 5. The description below illustrates a preferred embodiment of that control process.

Control box 20 houses a CPU that operates under program control. In one embodiment, the CPU uses three sources of information to decide when to initiate (i.e., open) the solenoid valve. It measures electromagnetic fields generated by the compressor's induction motor, acoustic signals, and the ambient temperature. All three measurements are amplitude based. Because the apparatus typically is either full on or full off, it typically only cares about peak amplitudes of each metric. The CPU uses the threshold data to ensure the mister runs at the most optimum time.

Temperature

Water based pre-cooling begins to lose efficiency the closer the ground water temperature is to the ambient temperature. Tests have shown that 78 degrees Fahrenheit to be the best all around temperature based cutoff. Thus, in this embodiment, if the temperature sensor reads less than 78 degrees Fahrenheit, the CPU will sense that and disable the unit (i.e., it will not allow the solenoid valve to open).

Acoustics

The acoustics section uses the amplitude of the sound waves generated by the running compressor and fan as a turn-on verification. When a predetermined appropriate noise threshold is met (as sensed by the acoustic detector and delivered to the CPU), the CPU will allow the system to arm (i.e., capable of turning on the solenoid valve if other parameters are met). This is a method the CPU uses to confirm the compressor is running. As indicated, having this threshold met alone will not turn the system on, it is used merely as a "go, no go" signal to the CPU.

EMF

When the compressor motor turns on, it generates strong EMF around its core. The CPU is equipped with an antenna system (EMF detector in FIG. 5) designed to pick up and measure these fields. Using EMF to gauge operation allows the unit to discriminate between local AC systems (when the system is installed on multiple compressor systems) as well as tell the CPU when it is the proper time to turn on the system. The system preferably should only run when the compressor is on.

Accordingly, in this embodiment, the CPU senses temperature, acoustics, and EMF. The CPU will only cause the solenoid valve to open if each of these metrics is met. In other words, the ambient air temperature must be at least 78 degrees Fahrenheit, the acoustic detector must be detecting a sufficient level of "noise", and the EMF detector must be detecting a sufficient level of EMF. If all three of these metrics is met, the CPU will issue a command to open the solenoid valve and allow water to traverse the valve and ultimately mist the air conditioner unit. If any one of these metrics is not met, the CPU will not open the solenoid valve, thereby preventing any water from traversing the valve.

Those skilled in the art will appreciate that other metrics can be used, including more, less, and/or different metrics. Likewise, variants of the preferred components of the system, as described below, are within the scope of the present invention.

Manifold

Manifold 50 preferably consists of three individual spray bars, each with three mister nozzles attached. The nozzles are rated for 5.4 gph @ 80 psi and have an orifice of 0.04 mm. While the manifold can be any shape, a preferred embodiment uses a flat side to host the nozzles. This flat surface enables a nozzle o-ring to properly seat between the nozzle and the side, so as to best prevent water leakage and provide optimal spray out of the nozzle. Additional spray bars can be added, as can spray bars with more (or less) mister nozzles attached. As will be appreciated by those skilled in the art, as mister nozzles are added, the flow rate increases.

Filters

The preferred filter 50 is made by Electrical Appliances Ltd. The filters are standard 10"×2" cylindrical cartridge filters often seen on ice makers. They have ½" npt ports and are made of LD polyethylene. The filtration media is Sodium Polyphosphate. Siliphos (for short) is a crystal-based media that dissolves slowly as water passes over it. When dissolved, its molecules prevent iron, calcium, magnesium (the constituents of water scale) from forming residue that could clog the system as well as damage the air conditioner's cooling system.

Valve

As described above, the valve (referred to above as the solenoid valve) is the heart of the CPU's control of the system because it controls when the water flows to the manifold. In embodiments where the mister system is solar powered (see FIG. 5), a special consideration is how much power the valve consumes. Traditional solenoid valves do not work well because they require power to be constantly applied to stay open. The valve preferably used uses a 22 mS+/−10% positive polarity pulse to latch the valve open and a 44 mS+/−10% negative polarity pulse to latch the valve closed. No other power is required to keep the valve open after the initial open signal is sent. When it is time to close the valve, a short negative going pulse is applied to the valve's solenoid and it latches closed.

Batteries

Batteries (see FIG. 5) are standard AA 1.5V nominal at 2,500 mAH units. Four batteries typically are required for operation, and with the solar array trickle charging the pack during daylight hours, the battery pack will last at least six months without needing to be replaced.

User Interface

Figure 5:
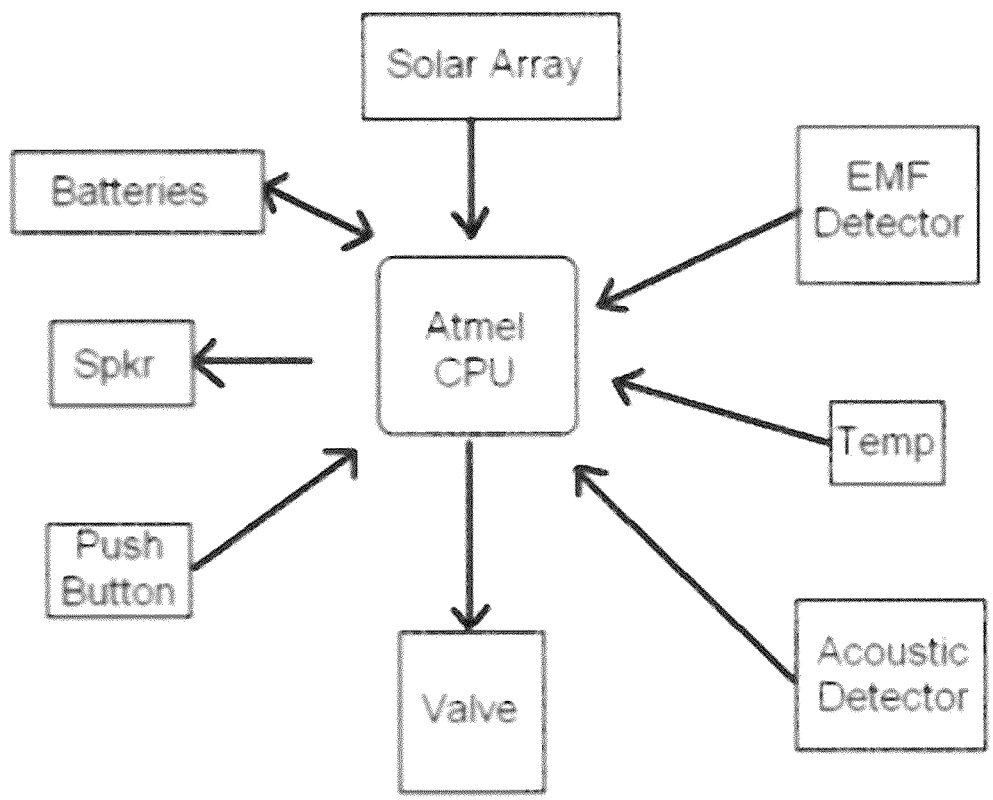
FIG. 5 illustrates control inputs used for controlling an embodiment of the present invention.

Interface with the system is achieved via one ductile weather proof rubberized push button switch mounted on the exterior of the control box (see FIG. 2) and a piezo speaker located within the control box (see FIG. 5). Using a system of button pushes and audio feedback, the user can set up the system. Other embodiments of the invention can use more push buttons for added functionality.

Solar Array

If used, the solar array preferably is a 9V 200 ma crystal metal matrix solar array that helps keep the batteries topped off and extends the system's autonomous run time. The CPU preferably has battery management/solar charger software installed, and it easily handles the job of battery pack maintenance and charging via solar energy.

CPU

As described above, the brain of the system preferably is an 8-bit Atmel microcontroller (the ATtinymega88 series). All functions of the controller are encoded and controlled via software. This not only allows for precision when it comes to control, measurements, and management, but it also lends itself to future proofing of the system. During the lifetime of the product, it may be desirable to fine tune and make changes to the control architecture and protocol of the system. Because the control box preferably has a programming port, that enables updates of previously manufactured systems to current firmware.

The following describes a preferred initial set up of the system. During initial set up, the system needs to be calibrated to the specific compressor system that it is installed on. Calibration ensures the system's function is tailored to each individual installation. Upon initial assembly and set up, the unit is powered on with the control button (see button 28 in FIG. 2) depressed. After 5 seconds, the unit is programmed to enter calibration mode. It will stay there until told otherwise. When the AC compressor turns on, the CPU will set its thresholds within approximately 10 seconds. When the CPU has enough information to set the proper thresholds, it will beep twice. The user then presses and holds the control button for 5 seconds and the thresholds become stored in memory and the setup mode is exited. A successful calibration will result in the unit making a series of beeps to indicate successful programming. The beeps will last 5 seconds allowing the user to back away from the unit before it begins misting. The CPU will now run its normal program. A filter timer is now started and the system will function autonomously until the filter timer reaches 0.

When it is time to change the filter cartridge, the system is programmed to alert the user via a series on audible beeps that run for 5 seconds every other hour (only during the day). When the user is ready to make the filter change, they will turn off the water source and disconnect the hose from the input port. The control button is pressed and held for 5 seconds. The unit will make a series of beeps to let the user know it is now in standby mode and is OK to change the filter. The user removes the old filter by unscrewing it from the control box and replaces it with a new filter. Once the water source is reconnected and turned on, the user presses and holds the control button for 5 seconds. The unit responds by emitting a series of beeps and the main program begins to run. The filter timer is also reset.

It will be apparent to one of skill in the art that described herein is a novel apparatus and method for increasing the efficiency of an air conditioning unit. While the invention has been described with references to specific preferred and exemplary embodiments, it is not limited to these embodiments. The invention may be modified or varied in many ways and such modifications and variations as would be obvious to one of skill in the art are within the scope and spirit of the invention and are included within the scope of the following claims.

The invention claimed is:

1. A controller for a misting apparatus, comprising:
an Electromagnetic Field (EMF) detector interface electrically coupled to the controller, the EMF detector configured to detect a change in electromagnetic field caused by operation of a motor in an air conditioner compressor;
a temperature sensor interface electrically coupled to a temperature sensor, the temperature sensor configured to sense a temperature near an air conditioner compressor;
an acoustic detector interface electrically coupled to an acoustic detector, the acoustic detector configured to detect sound waves generated by the air conditioner compressor; and
a processing device coupled to the EMF detector interface, the temperature sensor interface, and the acoustic detector interface, the processing device configured to determine when the motor of the air conditioner compressor is active in response to detected EMF and sound waves, and further configured to determine whether to activate the misting apparatus in response to the determination that the air conditioner compressor is active and in response to a determination that the temperature near the air conditioner compressor exceeds a predetermined threshold.

2. The controller of claim 1, the processing device is further configured to determine when the motor of the air conditioner compressor is active without a direct electrical connection to the air conditioning compressor.

3. The controller of claim 1, further comprising a battery coupled to the processing device and a solar array coupled to the battery, wherein the solar array is configured to electrically charge the battery and the battery is configured to supply power to the processing device.

4. The controller of claim 1, wherein the processing device is further configured to generate a command to activate the misting apparatus in response to the determination that the air conditioner compressor is active and in response to the determination that the temperature near the air conditioner compressor exceeds the predetermined threshold.

5. The controller of claim 1, wherein the processing device further comprises a calibration input for setting the thresholds for EMF, acoustic energy, and temperature readings associated with a specific air conditioner compressor.

6. The controller of claim 1, further comprising a user interface coupled to the processing device configured to receive threshold setup commands from a user.

7. A method for increasing the efficiency of an air conditioner comprising the steps of:
detecting, using an electromagnetic field (EMF) detector, a change in electromagnetic field caused by operation of a motor in an air conditioner compressor;
sensing, using a temperature sensor, a temperature near an air conditioner compressor;
detecting, using an acoustic detector, sound waves generated by the air conditioner compressor;
determining, using a processing device, when the motor of the air conditioner compressor is active in response to detected EMF and sound waves; and
determining, using the processing device, whether to activate a misting apparatus in response to the determination that the air conditioner compressor is active and in response to a determination that the temperature near the air conditioner compressor exceeds a predetermined threshold.

8. The method of claim 7, wherein determining when the motor of the air conditioner compressor is active is performed without a direct electrical connection to the air conditioning compressor.

9. The method of claim 7, further comprising electrically charging, using a solar array, a battery coupled to the processing device, the battery configured to supply power to the processing device.

10. The method of claim 7, further comprising actuating a valve configured to activate the misting apparatus in response to the determination that the air conditioner compressor is active and in response to the determination that the temperature near the air conditioner compressor exceeds the predetermined threshold.

11. The method of claim 7, further comprising calibrating the processing device to set the thresholds for EMF, acoustic energy, and temperature readings associated with a specific air conditioner compressor.

12. The method of claim 7, further comprising receiving threshold setup commands from a user interface coupled to the processing device.

* * * * *